United States Patent
Jochum

(10) Patent No.: US 9,987,467 B2
(45) Date of Patent: Jun. 5, 2018

(54) PORT FOR A CATHETER

(71) Applicant: Fresenius Kabi Deutschland GMBH, Bad Homburg (DE)

(72) Inventor: Christoph Jochum, Nidderau (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 56 days.

(21) Appl. No.: 15/122,768

(22) PCT Filed: Feb. 3, 2015

(86) PCT No.: PCT/EP2015/052115
§ 371 (c)(1),
(2) Date: Aug. 31, 2016

(87) PCT Pub. No.: WO2015/135693
PCT Pub. Date: Sep. 17, 2015

(65) Prior Publication Data
US 2017/0072169 A1   Mar. 16, 2017

(30) Foreign Application Priority Data
Mar. 11, 2014 (EP) .................................. 14158846

(51) Int. Cl.
*A61M 25/04* (2006.01)
*A61M 39/02* (2006.01)

(52) U.S. Cl.
CPC ........ *A61M 25/04* (2013.01); *A61M 39/0208* (2013.01); *A61M 2039/027* (2013.01);
(Continued)

(58) Field of Classification Search
CPC .............. A61M 25/04; A61M 39/0208; A61M 2039/0223; A61M 2039/0235; A61M 2039/0258; A61M 2039/027
(Continued)

(56) References Cited

U.S. PATENT DOCUMENTS 4,704,103 A * 11/1987 Stober .................. A61M 39/12
604/175
2003/0199853 A1* 10/2003 Olsen .................... A61M 39/12
604/535
(Continued)

FOREIGN PATENT DOCUMENTS

EP        2098197 A1    9/2009
WO    WO2005/032645 A2    4/2005

OTHER PUBLICATIONS

International Search Report for International Application No. PCT/EP2015/052115, dated Apr. 2, 2015.
(Continued)

*Primary Examiner* — Manuel Mendez
(74) *Attorney, Agent, or Firm* — Cook Alex Ltd.

(57) ABSTRACT

A port (1) for a catheter comprises: a housing (10) having at least two fixing holes (120, 20A, 120B); a cavity (140) arranged in the housing (10) for receiving a fluid; a membrane (13) attached to the housing (10) and arranged on an opening (102) of the housing (10) for sealing the opening (102) such that the cavity (140) is enclosed in the housing (10) in a fluid-tight manner; and a catheter (2) connected to the housing (10), the catheter (2) being in fluid connection with the cavity (140). In addition a yarn guide device (16) is arranged on the housing (10) in between the membrane (13) and the catheter (2), the yarn guide device (16) comprising a guide channel (161) formed in the housing (10) for receiving a yarn (3) for fixing the port (1) to an object and for guiding the yarn (3) in between the membrane (13) and the catheter (2). In this way a port is provided which allows for an easy fixing of the port by means of a yarn and reduces the risk of the yarn interfering with the catheter attached to the port.

6 Claims, 2 Drawing Sheets

(52) U.S. Cl.
CPC ............... *A61M 2039/0223* (2013.01); *A61M 2039/0235* (2013.01); *A61M 2039/0258* (2013.01)

(58) Field of Classification Search
USPC .. 604/539, 174, 175, 288.01, 288.02, 93.01, 604/502; 128/DIG. 26
See application file for complete search history.

(56) References Cited

U.S. PATENT DOCUMENTS

| | | | |
|---|---|---|---|
| 2006/0047248 A1* | 3/2006 | Poutiatine | A61M 5/14276 604/174 |
| 2007/0149947 A1 | 6/2007 | Byrum | |
| 2014/0024998 A1 | 1/2014 | Prosl et al. | |

OTHER PUBLICATIONS

Written Opinion of the International Searching Authority for International Application No. PCT/EP2015/052115, dated Apr. 2, 2015.

\* cited by examiner

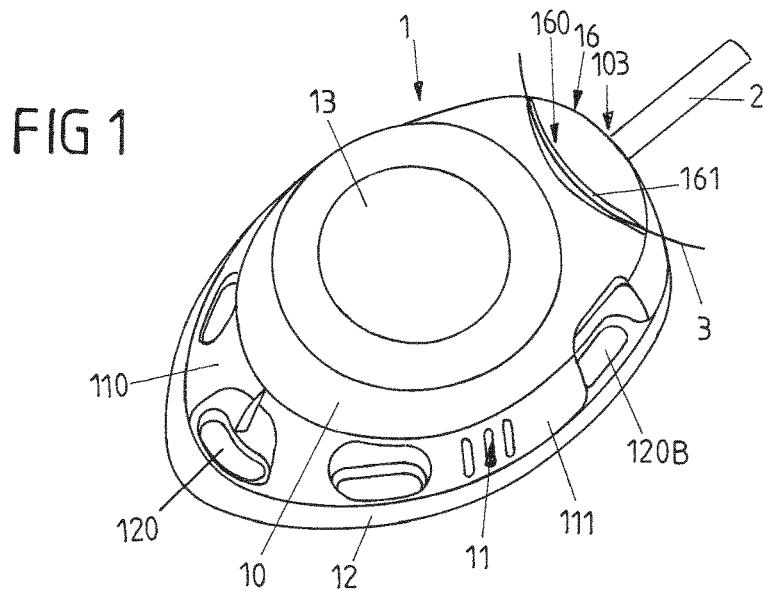
FIG 1
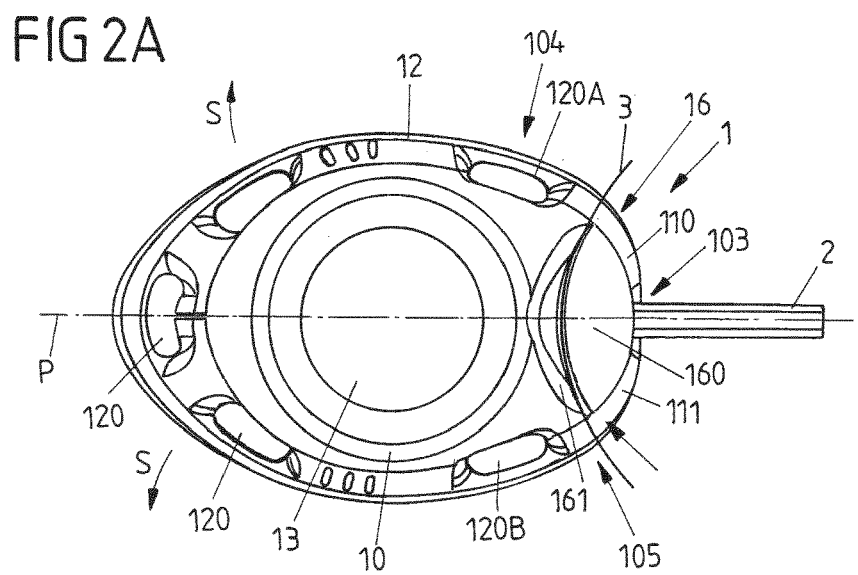
FIG 2A
FIG 2B
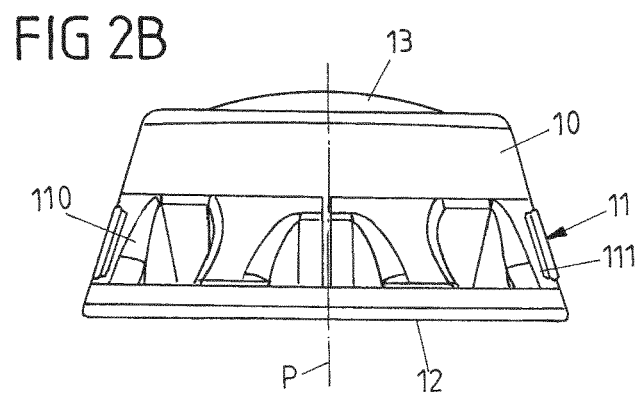

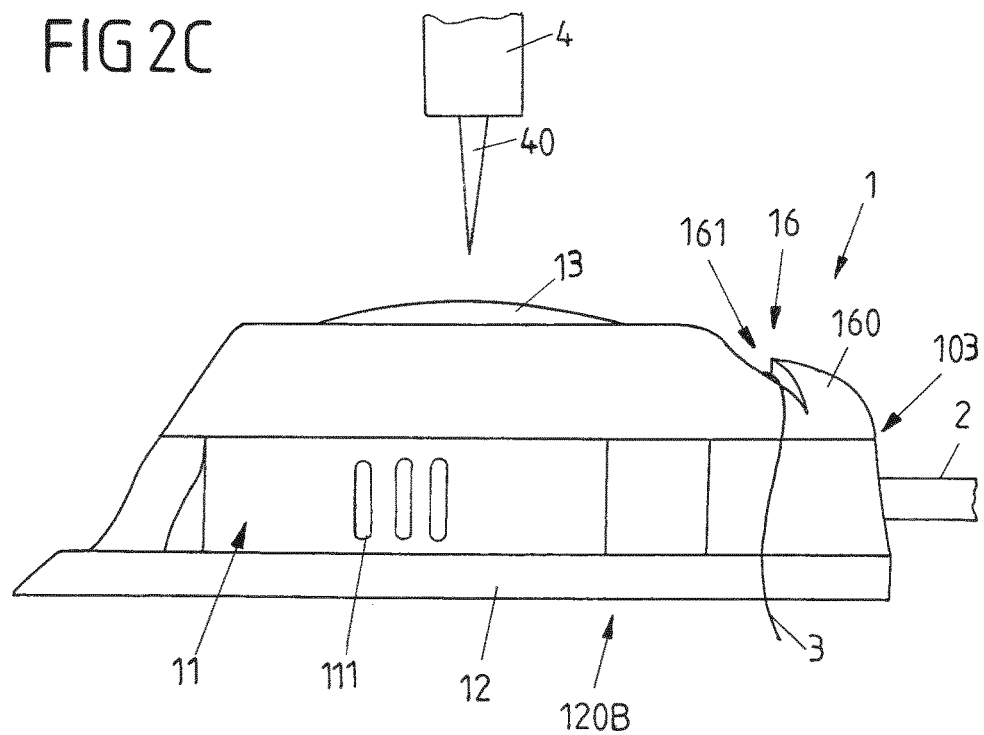
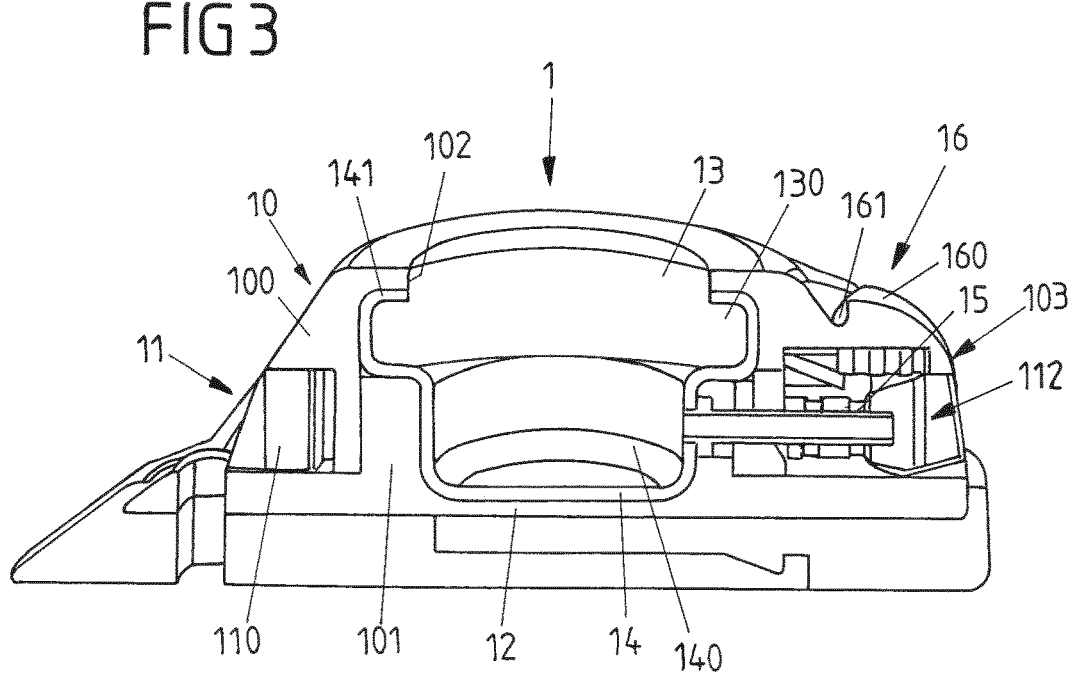

PORT FOR A CATHETER

The present application is the U.S. National Stage of PCT International Patent Application No. PCT/EP2015/052115, filed Feb. 3, 2015, which claims the benefit of and priority to European Patent Application No. 14158846.7, filed Mar. 11, 2014, the contents of both of which are hereby incorporated herein by reference.

The invention relates to a port for catheter according to the preamble of claim 1.

A port of this kind comprises a housing, a cavity arranged in the housing for receiving a fluid, a membrane attached to the housing and arranged on an opening of the housing for sealing the opening such that the cavity is enclosed in the housing in a fluid-tight manner, and a catheter connected to the housing, the catheter being in fluid connection with the cavity.

A port of this kind, as it is known for example from EP 1 675 641 B1, can be implanted into a patient in that it for example is inserted and fixed subcutaneously beneath the skin of a patient. The port herein serves for infusing a medical drug, a blood product, a nutritional fluid or another medical fluid into the venous or arterial system of a patient. By means of the port a medical fluid can be administered to a patient in a repeated fashion over a rather long period of time. Because the port is completely implanted under the skin of a patient, the risk for infections is reduced, and a medical fluid can be administered to the patient for treatment over a long period of time without the patient having to be stationary in a hospital and without the port impacting the everyday life of the patient.

During an infusion, a medical fluid is guided from the cavity enclosed in the housing via the catheter to a location of action in the patient, for example into the venous or arterial system of the patient. The catheter herein together with the port is implanted into the patient and is placed in the patient such that the medical fluid can be transported to the predefined location of action in the patient.

For implanting the port into a patient, the port is inserted for example subcutaneously under the skin of a patient. Herein, for fixing the port in its location, the housing of the port conventionally comprises a multiplicity of fixing holes through which a yarn extends by which the port may be fixed for example to a subcutaneous fascia of the patient. The port, via the yarn extending through the fixing holes, hence is held in place.

In an implanted state the catheter extends from the port towards a location of action to which the medical fluid shall be delivered. When fixing the port by means of the yarn it must be made sure that the yarn does not interfere with the catheter and in particular does not reduce the guiding lumen of the catheter or even pinch off the catheter.

In addition, with conventional arrangements of fixing holes it sometimes is complicated to fix a port in particular in small-sized skin pockets. In particular, in small-sized skin pockets it sometimes is difficult to insert a yarn through all fixing holes, or it becomes necessary to use multiple yarn sections because not all fixing holes can be accessed with a single yarn.

It is an object of the instant invention to provide a port which allows for an easy fixing of the port by means of a yarn and reduces the risk of the yarn interfering with the catheter attached to the port.

This object is achieved by means of a port comprising the features of claim 1.

Accordingly, the port comprises a yarn guide device arranged on the housing in between the membrane and the catheter, the yarn guide device comprising a guide channel formed in the housing for receiving a yarn for fixing the port to an object and for guiding the yarn in between the membrane and the catheter.

The instant invention is based on the idea to provide a yarn guide device for guiding the yarn on the housing between opposite sides of the housing. Herein, the yarn guide device with its guide channel is arranged spatially between the membrane and the catheter and hence passes from one side of the housing in between the membrane and the catheter towards another side of the housing. By placing the yarn in the guide channel of the yarn guide device it can be made sure that the yarn does not interfere either with the membrane or with the catheter. The yarn hence is securely arranged on the housing in a defined manner, making it possible to use one yarn to fix the port for example in a patient.

The housing, in one embodiment, comprises a base plate in which at least two fixing holes are formed. The base plate is arranged on a side of the housing opposite the membrane and hence forms a bottom of the port.

The catheter for example is fixed to a first end of the housing and extends sideways from the housing. For connecting the catheter to the housing, for example a connector may be provided to which the catheter may be (releasably) attached in a clamping fashion and which provides a fluid connection for connecting the catheter to the cavity enclosed in the housing.

In one embodiment, the guide channel extends across the first end of the housing in between a first side of the housing and a second side of the housing opposite the first side, such that the guide channel runs across the first end of the housing in between the first side and the second side and hence provides a defined path for the yarn in between the first side and the second side. The guide channel runs across the first end in between the catheter and the membrane and hence allows to place the yarn on the housing without interfering with the membrane or the catheter.

The guide channel, in a beneficial embodiment, is formed by an indentation formed in the housing. The guide channel, thus, extends in a groove-like fashion on the housing such that the yarn may be placed in the guide channel by simply inserting it into the indentation forming the guide channel.

In another embodiment, an elevation is provided on the housing bounding the guide channel towards the catheter. The elevation protrudes towards the outside and forms a barrier bounding the guide channel towards the catheter. By means of such additional elevation it can be made sure that the yarn cannot slide out of the guide channel towards the catheter such that the yarn is securely held in the guide channel of the yarn guide device.

In addition, by means of such elevation it can be made sure that a puncturing needle by means of which the membrane shall be punctured for inserting a medical fluid into the cavity enclosed in the housing cannot slide, when missing the membrane, along the housing towards the catheter, potentially bearing the risk of damaging the catheter. If a puncturing needle misses the membrane on a side of the membrane facing the catheter and instead of the membrane hits the housing, the puncturing needle will slide into the indentation of the yarn guide device and hence is deflected from the catheter.

In particular, the guide channel of the yarn guide device and the elevation bounding the guide channel may extend in a direction transverse to a (virtual) line connecting the membrane and the catheter, such that a puncturing needle is deflected in a transverse direction when sliding from the membrane towards the catheter.

By means of the yarn guide device hence an additional protection against damaging the catheter by means of the puncturing needle is provided.

The port may comprise an insertion piece inserted into the housing and forming the cavity. The insertion piece may function as an inlay providing the cavity, wherein the insertion piece may be made for example of a material resistant against a medical fluid to be used in the port, for example a metallic material or a ceramic material. The insertion piece may for example be formed such that it holds the membrane in a positive locking manner. For example, the insertion piece at its upper rim may have a groove-like shape into which the membrane is inserted in a positive locking manner and hence is held on the housing of the port.

The idea underlying the invention shall subsequently be described in more detail with respect to the embodiments shown in the figures. Herein:

FIG. 1 shows a perspective view of a port;
FIG. 2A shows a top view of the port;
FIG. 2B shows a front view of the port;
FIG. 2C shows a side view of the port; and
FIG. 3 shows a sectional view along the plane of symmetry as indicated in FIG. 2A.

FIGS. 1 to 3 show a port 1 constituted to be implanted into a patient. The port 1 comprises a housing 10 and a membrane 13 attached thereto. A catheter 2 is attached to the housing 10 and is in fluid connection with a cavity 140 enclosed in the housing 10.

The functional construction of the port 1 can best be seen from the sectional view of FIG. 3. The housing 10 comprises two housing parts 100, 101 which firmly are connected to each other and together form a cavity 140 for holding a medical fluid. A first housing part 100 herein has an opening 102 at the top of the port 1 in which the membrane 13 is arranged in a fluid-tight manner. A second housing part 101 forms a base plate 12 at the bottom of the port 1. The cavity 140 is provided in an insertion piece 14, formed from a material resistant against the medical fluid to be inserted into the cavity 140, for example from metal or a ceramic material. The membrane 13, by means of a circumferential edge 130, is in positive locking engagement with an upper rim section 141 of the insertion piece 14, wherein the rim section is shaped in a groove-like manner and receives the edge 130 of the membrane 13 in a clamping fashion.

Attached to the second housing piece 101 is a connector 15 for attaching the catheter 2 to the housing 10 and the cavity 140 arranged therein. The catheter 2 may be placed on the connector 15 and, in a connected state, is held on the connector 15 by means of a fixing device 11 comprising two clamping levers 110, 111. The clamping levers 110, 111, as indicated in FIG. 2A, are pivotably arranged on the housing 10 and may be pivoted along pivoting directions S with respect to the housing 10, wherein in a pivoted state—in which the clamping levers 110, 111 are pivoted out from the housing 10 in the pivoting direction S such that they extend away from the housing 10—the catheter 2 can be inserted into an opening 112 formed between the clamping levers 110, 111 and can be placed on the connector 15. By pivoting the clamping levers 110, 111 against the pivoting direction S, the catheter 2 are clamped against the connector 15 such that, in a clamped state in which the clamping levers 110, 111 assume the position shown in FIG. 2A and hence are arranged on the housing 10 in a compact fashion, the catheter 2 is fixedly held on the connector 15.

The base plate 12 comprises five fixing holes 120, 120A, 120B which serve to fix the port 1 when it is implanted into a patient such that via a yarn the port 1 can be fixed for example to a section of a fascia subcutaneously in a patient.

On the housing 10 a yarn guide device 16 is arranged, the yarn guide device 16 comprising a guide channel 161 formed by an indentation in the surface of the housing 10. The yarn guide device 16 serves to guide the yarn 3 from a first side 104 of the housing 10 towards a second side 105 of the housing 10. The guide channel 161 of the yarn guide device 16 herein extends across a front end 103 of the housing 10 of the port 1 at which the catheter 2 is arranged. The guide channel 161 is placed in between the membrane 13 and the catheter 2 and extends substantially transverse to a (virtual) line connecting the membrane 13 and the catheter 2, namely perpendicular to a plane of symmetry P of the port 1, as indicated in FIG. 2A.

The guide channel 161, towards the catheter 2, is bound by an elevation 160 protruding outwardly from the housing 10.

The yarn guide device 16 with its guide channel 161 serves, as indicated, for guiding the yarn 3 from the first side 104 of the housing 10 to the second side 105 of the housing 10. By means of the yarn guide device 16 the yarn 3 may be placed on the housing 10 in a defined manner in between the membrane 13 and the catheter 2 such that it does not interfere with the membrane 13 or the catheter 2. In particular, it is prevented that the yarn 3 runs across the catheter 2, hence alleviating the risk of pinching off the catheter 2 by means of the yarn 3.

Because the yarn 3 may be placed across the housing 10 in between the membrane 13 and the catheter 2 it becomes possible to use a single yarn section for fixing the port 1 to a patient. This allows to fix the port 1 also in a tight skin pocket.

For this, the yarn 3 is placed on the yarn guide channel 161 and is fixed to tissue of a patient on both sides 104, 105 of the port 1 such that the port 1 is fixed by means of the yarn 3 within the patient. In this case the fixing holes 120, in particular the two fixing holes 120A, 120B at the front end 103 of the port 1, not necessarily must be used. A fixing of the port 1 to tissue of a patient is possible simply by placing a yarn 3 through the yarn guide device 16 and fixing it to the tissue on both sides 104, 105 of the port 1.

The yarn guide 16 furthermore reduces the risk that a puncturing needle 4, as indicated in FIG. 2C, may slide along the housing 10 towards the catheter 2, which potentially may bear the risk of damaging the catheter 2 with the needle 40. Namely, if it is tried to puncture the membrane 3 by means of the needle 40, but if the membrane 13 is missed and rather the housing 10 is hit on a side of the membrane 13 towards the catheter 2, the needle 40 can slide along the housing 10 only until it reaches the indentation of the guide channel 161 by means of which it is deflected in a transverse direction such that it cannot impinge on the catheter 2.

The idea underlying the invention is not limited to the embodiments described above, but may also be implemented in an entirely different fashion.

For example, the yarn guide device with its guide channel may have a different shape. For example the yarn guide device may have a different direction of extension.

The yarn guide device may also be formed by a longitudinally extending hole formed in and extending through the housing.

In addition, more than one guide channel may be provided on the housing, hence defining different paths on the housing.

LIST OF REFERENCE NUMERALS

1 Port
10 Housing
100, 101 Housing part
102 Opening
103 Front end
104 First side
105 Second side
11 Fixing device
110, 111 Clamping levers
112 Opening
12 Base plate
120, 120A, 120B Fixing holes
13 Membrane
130 Edge
14 Insertion piece (trough)
140 Cavity
141 End section
15 Connector
16 Yarn guide device
160 Elevation
161 Guide channel (indentation)
2 Catheter
3 Yarn
4 Puncturing device
40 Needle
P Plane of symmetry
S Pivoting direction

The invention claimed is:

1. A port for a catheter, comprising:
   a housing,
   a cavity arranged in the housing for receiving a fluid,
   a membrane attached to the housing and arranged on an opening of the housing for sealing the opening such that the cavity is enclosed in the housing in a fluid-tight manner,
   a catheter connected to the housing, the catheter being in fluid connection with the cavity, and
   a yarn guide device arranged on the housing in between the membrane and the catheter, the yarn guide device comprising a guide channel formed in the housing for receiving a yarn for fixing the port to an object and for guiding the yarn in between the membrane and the catheter,
   wherein the housing is formed by a first housing part and a second housing part, the first housing part forming said opening in which the membrane is received and the second housing part forming a base plate of the housing,
   wherein a first group of fixing holes for receiving a yarn is formed in the base plate on a first side of the housing and a second group of fixing holes for receiving a yarn is formed in the base plate on a second side of the housing,
   wherein the guide channel of the yarn guide device is formed as an indentation in the first housing part and extends from the first side to the second side of the housing.

2. The port according to claim 1, characterized in that a yarn is placed in the guide channel of the yarn guide device.

3. The port according to claim 1, characterized in that the catheter is fixed to a first end of the housing.

4. The port according to claim 1, characterized in that the yarn guide device comprises an elevation bounding the guide channel towards the catheter.

5. The port according to claim 1, characterized in that an insertion piece is arranged in the housing and forms the cavity.

6. The port according to claim 5, characterized in that the membrane is attached to the insertion piece in a positive locking manner.

* * * * *